(12) United States Patent
Dahmen et al.

(10) Patent No.: US 9,763,559 B2
(45) Date of Patent: Sep. 19, 2017

(54) ENDOSCOPE

(75) Inventors: Jan Dahmen, Seitingen-Oberflacht (DE); Elmar Teichtmann, Eppingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 523 days.

(21) Appl. No.: 12/856,325

(22) Filed: Aug. 13, 2010

(65) Prior Publication Data

US 2011/0040148 A1    Feb. 17, 2011

(30) Foreign Application Priority Data

Aug. 14, 2009   (DE) .................... 10 2009 037 318

(51) Int. Cl.
 *A61B 1/04* (2006.01)
 *A61B 1/00* (2006.01)
 *G02B 23/24* (2006.01)
 *A61B 1/07* (2006.01)

(52) U.S. Cl.
 CPC ...... *A61B 1/00071* (2013.01); *A61B 1/00137* (2013.01); *G02B 23/2476* (2013.01); *A61B 1/07* (2013.01)

(58) Field of Classification Search
 CPC ............ A61B 1/00137; A61B 1/00142; A61B 1/00195; A61B 1/00071; A61B 1/121
 USPC ................. 600/114, 119, 121–125, 133, 136
 See application file for complete search history.

(56) References Cited

U.S. PATENT DOCUMENTS

| | | | | |
|---|---|---|---|---|
| 2,975,785 A | * | 3/1961 | Sheldon ............ | A61B 1/00165 277/634 |
| 4,063,796 A | * | 12/1977 | Hiltebrandt ........... | G02B 23/16 359/506 |
| 4,390,012 A | * | 6/1983 | Mizumoto ............ | G02B 23/26 385/117 |
| 4,779,613 A | * | 10/1988 | Hashiguchi ........ | A61B 1/00179 359/512 |
| 4,813,400 A | * | 3/1989 | Washizuka ............... | G02B 6/04 385/117 |
| 5,601,525 A | * | 2/1997 | Okada ........................... | 600/160 |
| 5,840,016 A | * | 11/1998 | Kitano et al. ................. | 600/159 |
| 6,419,628 B1 | * | 7/2002 | Rudischhauser et al. .... | 600/133 |
| 2002/0128539 A1 | * | 9/2002 | Higuma ............ | A61B 1/00188 600/133 |
| 2006/0020165 A1 | * | 1/2006 | Adams ......................... | 600/121 |

(Continued)

FOREIGN PATENT DOCUMENTS

DE         7520162 U     10/1975
DE       19713275 A1    10/1998

*Primary Examiner* — Alexandra Newton
(74) *Attorney, Agent, or Firm* — Whitmyer IP Group LLC

(57) ABSTRACT

An endoscope with an instrument housing and with a shaft that is mounted on the distal end of the instrument housing and consists of an outer tube and an inner tube that is mounted at least partly in the outer tube, so that the outer tube and the inner tube are mounted on the instrument housing so that they can move with respect to one another in the axial direction of the shaft. To provide an endoscope that ensures a constantly fluid-tight relative motion of the two shaft tubes with respect to one another, it is proposed with the invention that the outer tube and inner tube should be mounted on the instrument housing so that they are mobile with respect to one another in the axial direction of the shaft by means of at least one flexible membrane.

11 Claims, 3 Drawing Sheets

(56) References Cited

U.S. PATENT DOCUMENTS

| 2006/0173242 A1* | 8/2006 | Navok | A61B 1/0011 |
| | | | 600/133 |
| 2007/0092188 A1* | 4/2007 | Hoefig | A61B 1/0011 |
| | | | 385/117 |
| 2008/0183037 A1* | 7/2008 | Ichikawa et al. | 600/104 |

* cited by examiner

ENDOSCOPE

CROSS-REFERENCE TO RELATED APPLICATIONS

The present application claims priority of German patent application No. 10 2009 037 318.7 filed on Aug. 14, 2009.

FIELD OF THE INVENTION

The invention relates to an endoscope having an instrument housing and a shaft that is positioned on the distal end of the instrument housing and consists of an outer tube and an inner tube positioned at least partly inside the outer tube, such that the outer tube and inner tube are mounted on the instrument housing so that they can move with respect to one another in the axial direction of the shaft.

BACKGROUND OF THE INVENTION

Endoscopes of this type are generally known in the art. The inner tube of the shaft serves for the insertion of optical components such as rod lenses. Between the inner tube of the shaft and the outer tube that surrounds the inner tube, it is customary to configure an open ring of space that serves, for instance, to contain optical fibers in order to conduct light to the distal end of the endoscope and thus to the surgical area that is to be investigated.

The endoscopes must be sterilized after each use, and for this purpose they are subjected in autoclaves to damp heat in the temperature range of 120 to 140 degrees C. Because of the different materials of the two tubes of the instrument shaft in connection with temperature fluctuations and/or because of temperature differences between the outer and inner tube, as a result of a delay in conducting heat from the outer tube to the inner tube, the outer tube and inner tube expand at different rates from the impact of these sometimes extreme temperatures. To allow a reduction of the resulting tensions between the tubes of the instrument shaft joined together on the distal end, the outer and inner tubes are mounted on the instrument housing so that they can move in relation to one another in the axial direction of the shaft.

A generic endoscope with length compensation at thermal impacts is known for instance from DE 197 13 275 A1. With this known structure the outer and inner tubes of the shaft forming one component insulated against fluids are each connected on the proximal end with a separate housing part of the instrument housing. To make possible the required axial relative movement between the outer and inner tubes, the two separate housing parts are floating mounted on one another by means of O-rings inserted between them.

This known construction has fully proven itself and allows a sufficient thermal length compensation of the shaft tubes, but the O-rings in particular at high thermal pressure during the cleaning of the endoscope do not ensure any permanent fluid-tight insulation of the instrument housing.

SUMMARY OF THE INVENTION

It is consequently the object of the invention to provide an endoscope that ensures a permanent fluid-tight relative movement of the two shaft tubes with respect to one another.

This object is achieved according to the invention in that the mutually movable mounting of the outer and inner tubes in the axial direction on the instrument housing occurs by means of at least one flexible membrane.

As a result of the inventive use of at least one membrane between the components that are to be connected, and because of the flexibility of the membrane, the relative movement between the two tubes of the instrument shaft becomes possible and at the same time a flexible connection is provided, which ensures a permanently fluid-tight connection even with frequent use.

According to a preferred embodiment of the invention it is proposed that the at least one flexible membrane should be a metal membrane. Corrosion-proof metallic membranes are distinguished in that they are permanently stable even with frequent use and many cleaning processes at high temperature exposures.

It is proposed with a practical embodiment of the invention that the instrument housing should include an external housing part connected with the proximal end of the outer tube and an internal housing part connected with the proximal end of the inner tube. The division of the instrument housing into an external and an internal housing part makes possible an especially variable configuration to produce the desired relative mobility between the two tubes of the instrument shaft.

According to a first embodiment of the invention it is proposed that the outer tube and the external housing part should be connected with one another by means of the at least one flexible membrane. In this embodiment the membrane connection between the external housing part and the outer tube, thanks to its flexibility, allows the temperature-dependent length modification of the outer tube and, connected with it, the relative movement to the inner tube.

According to a second embodiment of the invention, it is proposed that the inner tube and the internal housing part should be connected with one another by means of the at least one flexible membrane. This embodiment can be applied alternatively or in addition to the placing of a membrane between the external housing part and the outer tube.

With a third inventive embodiment it is proposed that the external housing part and the internal housing part should be connected with one another by means of the at least one flexible membrane. With this embodiment the relative mobility between the two tubes of the instrument shaft is made possible because the two tubes are each connected in fluid-tight manner and firmly with their related housing parts and the flexible membrane is positioned between the two housing parts, each of which is provided with a tube. This embodiment makes possible the installation of the complete unit consisting of outer tube and external housing part on the one hand, and inner tube and internal housing part on the other hand, which are connected with one another by means of the flexible membrane between the external housing part and the internal housing part.

Placing the membrane between the external housing part and the outer tube occurs according to a first practical embodiment of the invention on the distal end of the area of the external housing part that is contiguous with the outer tube. According to an alternative embodiment for positioning the membrane between the external housing part and the outer tube, it is proposed that the membrane should be positioned on the proximal end of the area of the external housing part that is contiguous with the outer tube.

To prevent the penetration of moisture and/or dirt between the components that are to be connected with one another, in particular in placing the flexible membrane further inward on the instrument housing, it is further proposed with the invention that in addition to the at least one membrane, at least one insulating element should be positioned between the components connected with one another by the membrane, so that the insulating element is preferably configured as an O-ring.

According to a preferred embodiment of the invention it is proposed that the at least one membrane should be configured as a thin-walled housing part that is manufactured in one piece together with the instrument housing. As a result of this unit construction of the membrane as part of the instrument housing, it is no longer necessary on the housing side to have a fluid-tight insulation for the component that is to be connected, of the kind that is to be configured on the free other end of the membrane for instance by welding, cementing, or soldering.

It is finally proposed with the invention that the at least one membrane should be configured as a separate component, which can be attached fluid-tight on the components that are to be connected with one another. Because of the configuration of the membrane as a separate component, it is possible, by appropriate choice of material, that is, independently of the material of the instrument housing, to select the material suited to the individual case that makes possible the desired relative movement between the components that are to be connected with one another.

Further properties and advantages of the invention can be seen from the associated drawings, in which four embodiments of an inventive endoscope are presented entirely by way of example, without restricting the invention to these embodiments.

DETAILED DESCRIPTION OF THE INVENTION

Figure 1:
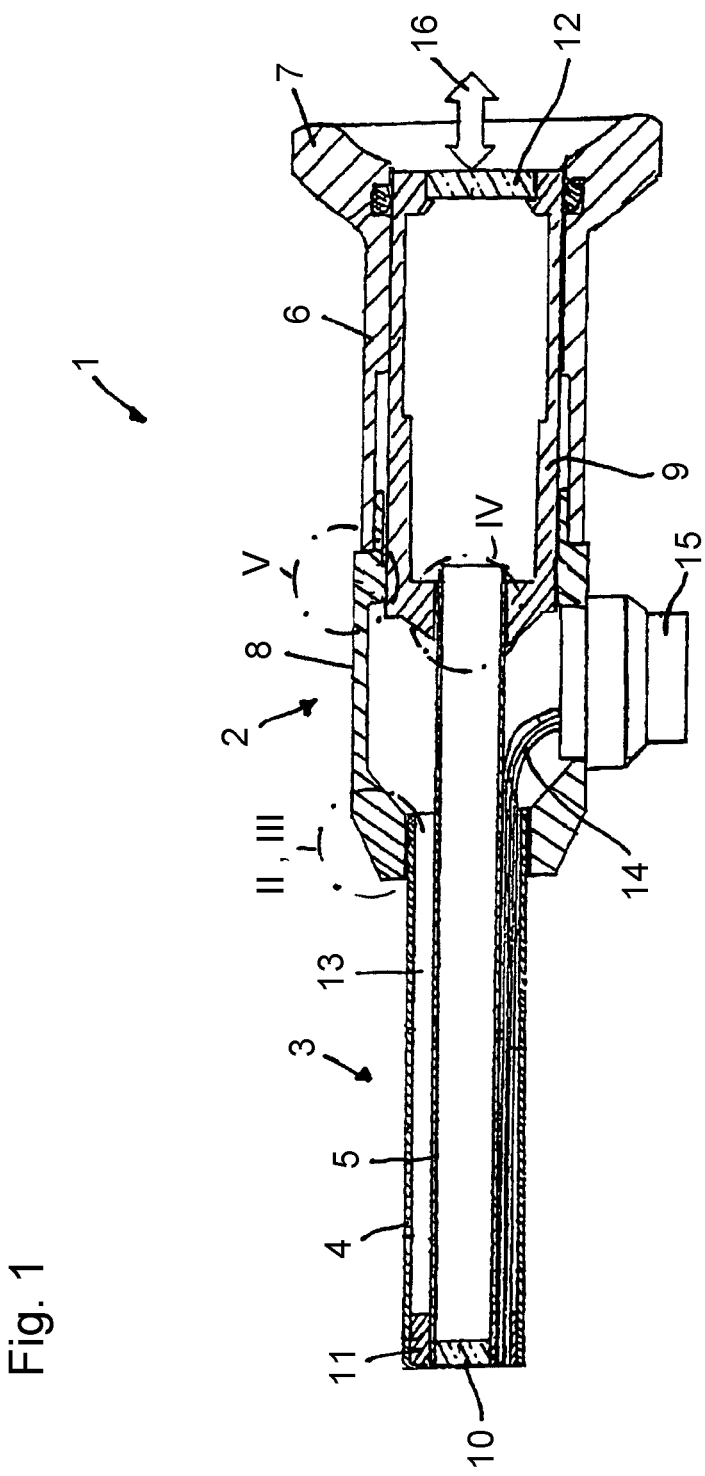
FIG. 1 shows a schematic side view of an inventive endoscope.

FIG. 1 shows an endoscope 1, which consists essentially of an instrument housing 2 and a hollow shaft 3 that is mounted on the distal end of the instrument housing 2 and that in turn consists of a hollow outer tube 4 and an inner tube 5 that is mounted in the outer tube 4. A lens head 6 with an eyepiece cup 7 is positioned on the proximal end of the instrument housing 2.

In the illustrated embodiment, the instrument housing 2 also consists of two parts, namely an external housing part 8 connected with the proximal end of the outer tube 4 and an internal housing part 9 connected with the proximal end of the inner tube 5.

The inner tube 5 of the shaft 3 serves for inserting optical components such as rod lenses for example. These optical components positioned inside the inner tube 5 are not illustrated, for reasons of greater clarity in the drawing. On the distal end the inner tube 5 is closed fluid-tight with a transparent disc 10 and connected fluid-tight with the distal end of the outer tube 4 by means of an insulation 11 configured, for instance, in ring shape.

On the proximal end the illustrated instrument housing 2 is closed by a transparent disc 12 positioned fluid-tight in the proximal end of the internal housing part 9.

Because of the essentially coaxial arrangement of the outer tube 4 and the inner tube 5, between the inside of the outer tube 4 and the outside of the inner tube 5 a ring-shaped space 13 is configured that serves, for instance, for the insertion of optical fibers 14, which are fed to the distal end of the shaft 3 by a connecting piece 15 in the instrument housing 2 in order to conduct light to the distal end of the endoscope 1 and thus to the operating area that is to be investigated. Corresponding light outlet openings are then configured in the insulation 11.

Because an endoscope 1 must be sterilized after each use, it is exposed in an autoclave to moist heat in the temperature range of 120 to 140 degrees C. Owing to this heating of the endoscope 1 and the subsequent cooling, because of the different materials of the two tubes 4 and 5 of the shaft 3, in connection with temperature fluctuations and/or on account of varying temperatures of the outer tube 4 and inner tube 5, and as a result of a delay in conducting heat from the outer tube 4 to the inner tube 5, the outer tube 4 and the inner tube 5 expand differently at these sometimes extreme temperature pressures. To be able to reduce the resulting tensions between the tubes 4 and 5 of the shaft 3 that are connected with one another on the distal end, the outer tube 4 and the inner tube 5 are mounted on the instrument housing 2 so that they can move with respect to one another in the axial direction of the shaft 3, as is shown by the double arrow 16 in FIG. 1.

As can be seen from FIGS. 2 through 5, the mounting of the outer tube 4 and of the inner tube 5 on the instrument housing 3 so that they are mobile with respect to one another in the axial direction of the shaft 3, is made possible by means of at least one flexible membrane 17, which is preferably configured as a corrosion-resistant metal membrane.

Figure 2:
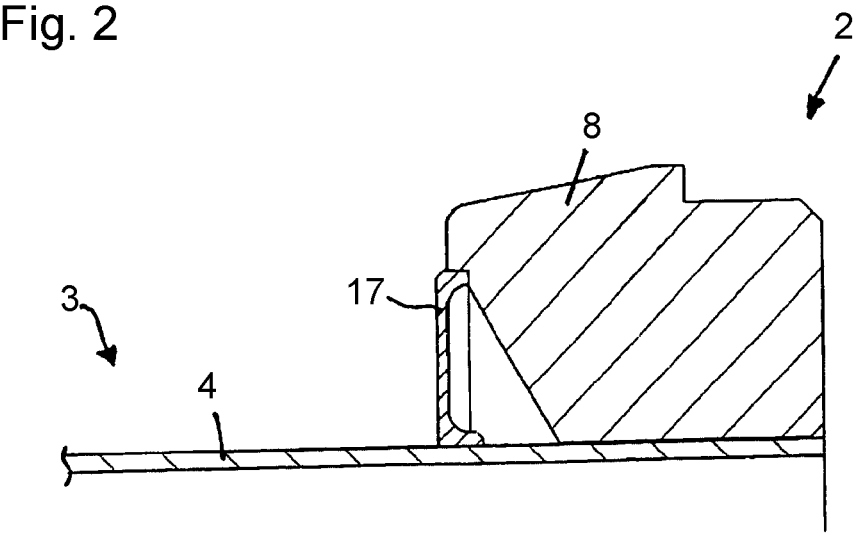
FIG. 2 shows an enlarged view of detail II from FIG. 1, depicting a first embodiment.

In the first embodiment, shown in FIG. 2, the membrane 17 connects the outer tube 4 and the external housing part 8 and thus, because of the flexibility of the membrane 17, makes possible a relative motion between the outer tube 4 and the instrument housing 2 and thus between the outer tube 4 and the inner tube 5. In this illustrated embodiment, the membrane 17 is positioned on the distal end of the area of the external housing part 8 that is contiguous with the outer tube 4.

Figure 3:
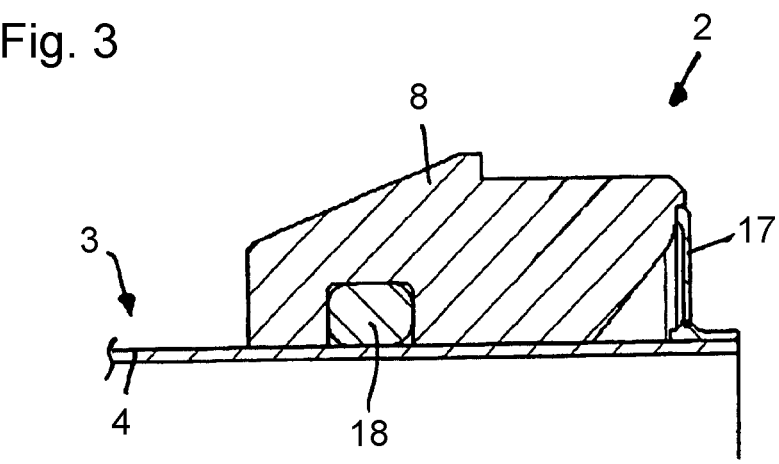
FIG. 3 shows an enlarged view of detail III from FIG. 1, depicting a second embodiment.

In the alternative second embodiment according to FIG. 3, the membrane 17 in turn connects the outer tube 4 and the external housing part 8 and thus, because of the flexibility of the membrane 17, makes possible a relative motion between the outer tube 4 and the instrument housing 2 and thus between the outer tube 3 and the inner tube 5; however, the membrane 17 in this embodiment is positioned on the proximal end of the area of the external housing part 8 that is contiguous with the outer tube 4.

The connection of the membrane 17 with the components that are to be connected with one another—the outer tube 4 and external housing part 8—occurs in both cases as fluid-tight, for example by welding, cementing, or welding.

To prevent the penetration of moisture and/or dirt between the components 4 and 8 that are to be connected with one another, in particular in placing the flexible membrane 17 further inward on the instrument housing as is shown in FIG. 3, in the illustrated embodiment, in addition to the membrane 17 an insulating element 18 is positioned between the components, outer tube 4 and external housing part 8, so that the insulating element 18 has the form of an O-ring.

Figure 4:
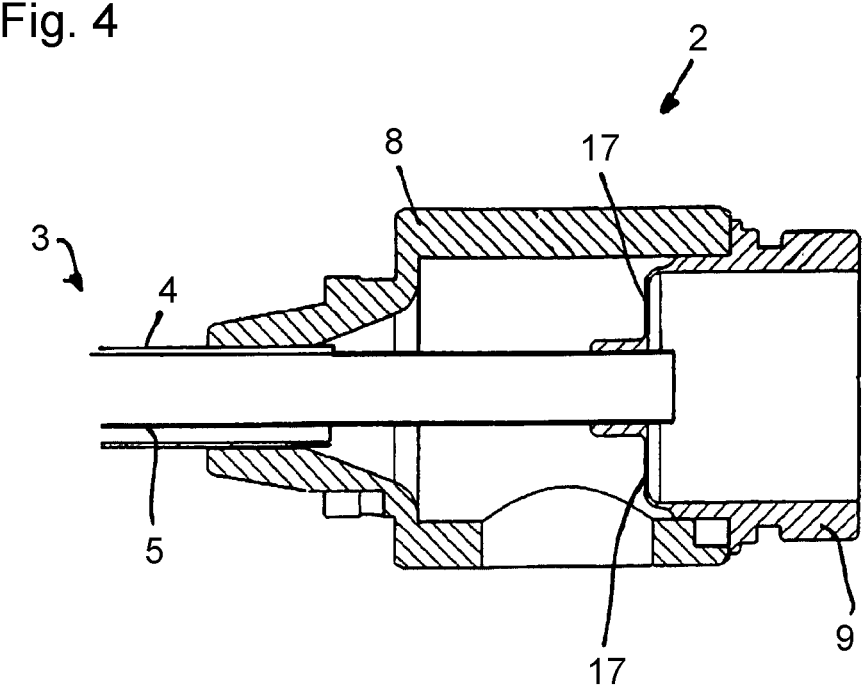
FIG. 4 shows an enlarged view of detail IV from FIG. 1, depicting a third embodiment.

FIG. 4 shows a third embodiment for positioning the membrane 17. In this embodiment the membrane 17 connects the inner tube 5 and the internal housing part 9 and thus, because of the flexibility of the membrane 17, makes possible a relative motion between the inner tube 5 and the instrument housing 2 and thus between the inner tube 5 and the outer tube 4.

The embodiments according to FIGS. 2 and 4 or FIGS. 3 and 4, either alternatively or else together, can be realized in one construction so that with the addition of the two embodiments, the outer tube 4 and the external housing part 8 as well as the inner tube 5 and the internal housing part 9 are each connected with one another by a flexible membrane 17.

Figure 5:
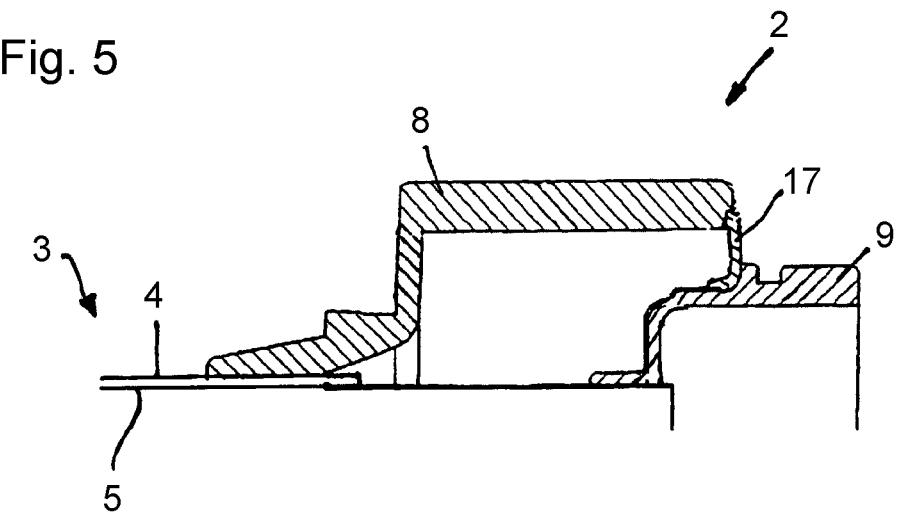
FIG. 5 shows an enlarged view of detail V from FIG. 1, depicting a fourth embodiment.

FIG. 5 shows finally an alternative fourth embodiment for placing the membrane 17 on the instrument housing 2. Unlike in the previously described embodiments, the at least one flexible membrane 17 in this embodiment does not connect the instrument housing 2 directly with one of the two tubes 4 and/or 5 of the shaft 6, but rather connects the external housing part 8 and the internal housing part 9 of the instrument housing 2.

In this embodiment the outer tube 4 and the external housing part 8 as well as the inner tube 5 and the internal housing part 9 are each connected fluid-tight together into one unit. The connection of the external housing part 8 and of the internal housing part 9 by the membrane 17 thus, because of the flexibility of the membrane 17 and of the firm connection of the tubes 4 and 5 in their particular housing parts 8 and 9, makes possible a relative motion between the inner tube 5 and the outer tube 4.

It is also true of the embodiments shown in FIG. 4 that the connection of the membrane 17 with the components that are to be connected with one another (the inner tube 5 and internal housing part 9 or external housing part 8 and internal housing part 9) is configured fluid-tight, for example by welding, cementing, or soldering.

Whereas in the embodiments shown in FIGS. 2, 3, and 5 the flexible membrane 17 is configured as a separate component, which is fastened fluid-tight to the two components that are to be connected with one another, for instance by welding, cementing, or soldering, FIG. 4 shows an embodiment in which the membrane 17 is configured on one side as a thin-walled housing part that is manufactured as a single unit with the internal housing part 9, so that it needs no particular fluid-tight insulation from the internal housing part.

An endoscope 1 of the aforementioned configuration is distinguished in that it ensures a permanent fluid-tight relative motion of the two tubes 4 and 5 of the shaft 3 with respect to one another, owing to the arrangement of the at least one flexible membrane 17 with its simple structure.

The invention claimed is:

1. An endoscope comprising:
   an instrument housing having an external housing part and an internal housing part disposed within the external housing part,
   a shaft that is mounted on a distal end of the instrument housing, the shaft having an outer tube and an inner tube mounted at least partly in the outer tube, a proximal end of the outer tube being mounted to a distal portion of the external housing part, a proximal end of the inner tube being mounted to the internal housing part, the outer tube and the inner tube being mounted on the instrument housing so that the tubes are movable in relation to one another in an axial direction of the shaft,
   at least one non-corrugated flexible membrane fastened to the outer tube and to only a proximal end of the distal portion of external housing part, the at least one flexible membrane providing a fluid-tight connection between the outer tube and the external housing part, the at least one flexible membrane having a length, in a longitudinal direction of the endoscope, that is shorter than a length of the distal portion of the external housing part,
   wherein the mounting of the outer tube and of the inner tube on the instrument housing so that the tubes are mobile with respect to one another occurs by means of the at least one flexible membrane.

2. The endoscope according to claim 1, wherein the inner tube and the internal housing part are connected to each other by at least another flexible membrane.

3. The endoscope according to claim 2, wherein the at least another flexible membrane is configured as a thin-walled housing part formed as a single unit with the instrument housing.

4. The endoscope according to claim 3, wherein the at least another flexible membrane is configured on one side as a single unit together with the instrument housing and is configured on another side with a free end fastened to the inner tube.

5. The endoscope according to claim 1, wherein the inner tube and the internal housing part are connected to each other by another flexible membrane.

6. The endoscope according to claim 1, wherein the external housing part and the internal housing part are connected to each other by another flexible membrane.

7. The endoscope according to claim 1, wherein in addition to the at least one membrane, at least one insulating element is positioned between the components that are connected with one another by the membrane.

8. The endoscope according to claim 7, wherein the at least one insulating element is configured as an O-ring.

9. The endoscope according to claim 1, wherein the at least one flexible membrane is a metal membrane.

10. An endoscope comprising:
    an instrument housing having an external housing part and an internal housing part disposed within the external housing part,
    a shaft that is mounted on a distal end of the instrument housing, the shaft having an outer tube and an inner tube mounted at least partly in the outer tube, a proximal end of the outer tube being connected to a distal portion of the external housing part, a proximal end of the inner tube being connected to the internal housing part, the outer tube and the inner tube being mounted on the instrument housing so that the tubes are movable in relation to one another in the axial direction of the shaft,
    at least one non-corrugated flexible membrane fastened to the outer tube and the external housing part, wherein the outer tube and the external housing part are connected with one another by the at least one flexible membrane, the at least one flexible membrane providing a fluid-tight connection between the outer tube and the external housing part, and
    at least another flexible membrane wherein the inner tube and the internal housing part are connected with one another by the at least another flexible membrane, the at least another flexible membrane providing a fluid-tight connection between the inner tube and the internal housing part,
    wherein the at least one flexible membrane and the at least another flexible membrane provide for the mounting of the outer tube and of the inner tube on the instrument housing so that the tubes are mobile with respect to one another, wherein in addition to the at least one flexible membrane, at least one insulating element is positioned between the outer tube and the external housing part.

11. The endoscope according to claim 10, wherein the at least one insulating element is configured as an O-ring.

\* \* \* \* \*